(12) United States Patent
Biederman, III et al.

(10) Patent No.: US 12,332,713 B2
(45) Date of Patent: *Jun. 17, 2025

(54) TWO-PHASE DEPLOYMENT-INITIATED WAKEUP MECHANISM FOR BODY-MOUNTABLE ELECTRONIC DEVICE

(71) Applicant: Dexcom, Inc., San Diego, CA (US)

(72) Inventors: William James Biederman, III, San Francisco, CA (US); Louis Hyunsuk Jung, Foster City, CA (US)

(73) Assignees: Verily Life Sciences LLC, Mountain View, CA (US); DexCom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/352,542

(22) Filed: Jul. 14, 2023

(65) Prior Publication Data

US 2024/0019920 A1 Jan. 18, 2024

Related U.S. Application Data

(63) Continuation of application No. 17/824,056, filed on May 25, 2022, now Pat. No. 11,747,877, which is a
(Continued)

(51) Int. Cl.
G06F 1/32 (2019.01)
G06F 1/3206 (2019.01)
(Continued)

(52) U.S. Cl.
CPC ........ *G06F 1/3206* (2013.01); *A61B 5/14532* (2013.01); *A61B 5/6833* (2013.01); *A61B 2560/0209* (2013.01)

(58) Field of Classification Search
CPC ............ G06F 1/3206; A61B 2560/0209
See application file for complete search history.

(56) References Cited

U.S. PATENT DOCUMENTS 9,146,605 B2 9/2015 Lee et al.
9,395,791 B2 7/2016 Yu et al.
(Continued)

FOREIGN PATENT DOCUMENTS

EP 1070479 A2 1/2001
WO 2015/126459 A1 8/2015

OTHER PUBLICATIONS

Microcontroller—Wikipedia, retrieved from the internet at <https://web.archive.org/web/20161027171629/https://en.wikipedia.org/wiki/Microcontroller> (Year: 2016).*
(Continued)

*Primary Examiner* — Stefan Stoynov
(74) *Attorney, Agent, or Firm* — Snell & Wilmer LLP

(57) ABSTRACT

The technology described herein is related to a two-phase deployment-initiated wakeup mechanism for a body-mountable electronic device. During a first phase of the two-phase wakeup mechanism, a motion sensor detects an acceleration event indicative of deployment of the device onto the body of the user. During a second phase of the two-phase mechanism, control circuitry can be adapted to be enabled by the acceleration event. Once enabled, the control circuitry can verify that the device has been launched onto the body of a user via a deployment applicator in which the device is retained until deployment. Once verified, the control circuitry can wake up the body-mountable electronic device by transitioning the device from a sleep state to a functional (or operational) state.

19 Claims, 11 Drawing Sheets

Related U.S. Application Data continuation of application No. 16/927,190, filed on Jul. 13, 2020, now Pat. No. 11,360,537, which is a continuation of application No. 16/168,527, filed on Oct. 23, 2018, now Pat. No. 10,712,797.

(60) Provisional application No. 62/577,323, filed on Oct. 26, 2017.

(51) Int. Cl.
*A61B 5/00* (2006.01)
*A61B 5/145* (2006.01)

(56) References Cited

U.S. PATENT DOCUMENTS

| | | | |
|---|---|---|---|
| 10,405,800 | B2 | 9/2019 | Ganton et al. |
| 10,441,180 | B2 | 10/2019 | Wang et al. |
| 2005/0000829 | A1 | 1/2005 | Morita et al. |
| 2007/0027381 | A1 | 2/2007 | Stafford |
| 2007/0163880 | A1 | 7/2007 | Woo et al. |
| 2011/0080349 | A1 | 4/2011 | Holbein et al. |
| 2013/0253472 | A1 | 9/2013 | Cabiri |
| 2014/0055387 | A1 | 2/2014 | Yeh |
| 2015/0018643 | A1 | 1/2015 | Cole et al. |
| 2016/0026212 | A1* | 1/2016 | Lee .................. G06F 1/3231 361/679.03 |
| 2016/0100778 | A1* | 4/2016 | Yi .................. A61B 5/6833 600/345 |
| 2016/0331283 | A1 | 11/2016 | Rao et al. |
| 2017/0185284 | A1 | 6/2017 | Bhavaraju et al. |
| 2019/0324520 | A1 | 10/2019 | Nakamura et al. |

OTHER PUBLICATIONS

Microprocessor—Wikipedia, retrieved from the internet at <https://web.archive.org/web/20161215164501/https://en.wikipedia.org/wiki/Microprocessor> (Year: 2016).*
Chinese Patent Application No. 201880069897.X, Office Action, 13 pages, Feb. 22, 2021.
European Patent Application No. 18870543.8, Extended European Search Report, 7 pages, Jun. 11, 2021.
International Application No. PCT/US2018/057130, International Search Report & Written Opinion, 7 pages, Dec. 27, 2018.
Phidgets, "Accelerometer Primer, https://web.archive.org/web/20121028143038/https://www.phidgets.com/docs/Accelerometer_Primer," 4 pages, Aug. 21, 2012.
Wikipedia, "g-force," https://web.archive.org/web/20160103163716/https://en.wikipedia.org/wiki/G-force, 12 pages, Dec. 8, 2015.

* cited by examiner

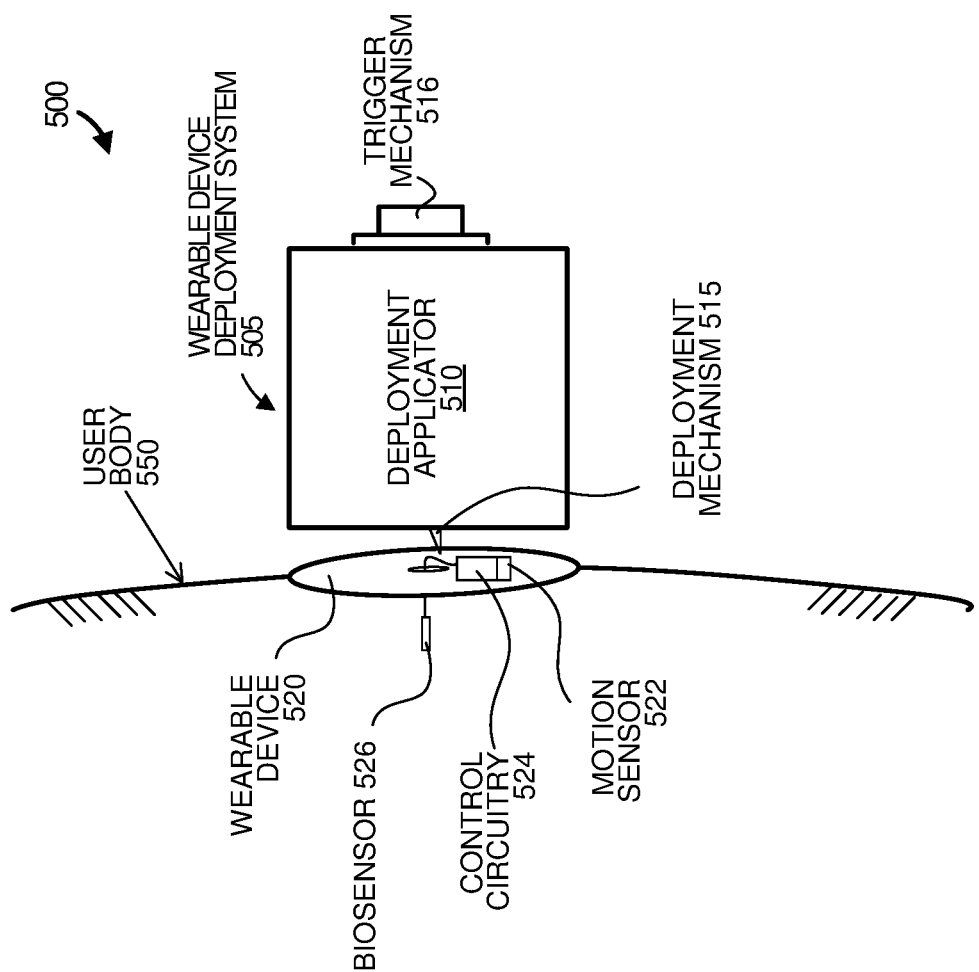

TWO-PHASE DEPLOYMENT-INITIATED WAKEUP MECHANISM FOR BODY-MOUNTABLE ELECTRONIC DEVICE

CROSS REFERENCE TO RELATED APPLICATIONS

This application is a continuation of and claims priority to U.S. patent application Ser. No. 17/824,056, filed on May 25, 2022, titled "Two-Phase Deployment-Initiated Wakeup Mechanism For Body-Mountable Electronic Device," now allowed; which is a continuation of U.S. patent application Ser. No. 16/927,190, filed on Jul. 13, 2020, titled "Two-Phase Deployment-Initiated Wakeup Mechanism For Body-Mountable Electronic Device," and issued as U.S. Pat. No. 11,360,537 on Jun. 14, 2022; which is a continuation of U.S. patent application Ser. No. 16/168,527, filed on Oct. 23, 2018, titled "Two-Phase Deployment-Initiated Wakeup Mechanism for Body-Mountable Electronic Device," and issued as U.S. Pat. No. 10,712,797 on Jul. 14, 2020; which claims priority to and benefit from U.S. Provisional Patent Application No. 62/577,323, filed on Oct. 26, 2017, titled "Two-Phase Deployment-Initiated Wakeup Mechanism for Body-Mountable Electronic Device"; each of which are expressly incorporated by reference herein.

BACKGROUND

Disposable electronic devices such as medical body-mountable (or wearable) devices, and the like, need to be small, low cost and energy efficient. These devices often include a variety of electronic components such as power sources, microcontrollers, sensors, etc. The power sources typically include non-replaceable batteries having limited capacities. Prior to deployment, a body-mountable device often remains unused for an extended period of non-operational time, e.g., transport, storage, etc. If power is enabled (even at reduced levels) during the non-operational time, then current leakage can significantly reduce the amount of energy available to the device during a functional (or operational) state. To overcome these current leakage problems, body-mountable devices are often designed with batteries having larger capacities. Unfortunately, the larger capacity batteries increase both the footprint or size of a body-mountable device and production costs.

To further improve energy efficiency, some body-mountable devices utilize low-power modes. Various mechanisms are utilized to wake the body-mountable devices up from a low-power mode, however, these wakeup mechanisms often require additional components that are expensive both in terms of increased production costs and increased footprint or size of the device. Regardless, many of the existing wakeup mechanisms are unreliable, e.g., prone to false wakeups.

Overall, the examples herein of some prior or related systems and their associated limitations are intended to be illustrative and not exclusive. Upon reading the following, other limitations of existing or prior systems will become apparent to those of skill in the art.

BRIEF DESCRIPTION OF THE DRAWINGS

In order to describe the manner in which the above-recited and other advantages and features can be obtained, a more particular description is set forth and will be rendered by reference to specific examples thereof which are illustrated in the appended drawings. Understanding that these drawings depict only typical examples and are not therefore to be considered to be limiting of its scope, implementations will be described and explained with additional specificity and detail through the use of the accompanying drawings.

FIGS. 5A, 5B and 5C depict diagrams illustrating an example operational environment during various stages of deploying a body-mountable electronic device retained in a mountable device deployment system onto a user body, according to some embodiments.

Figure 1:
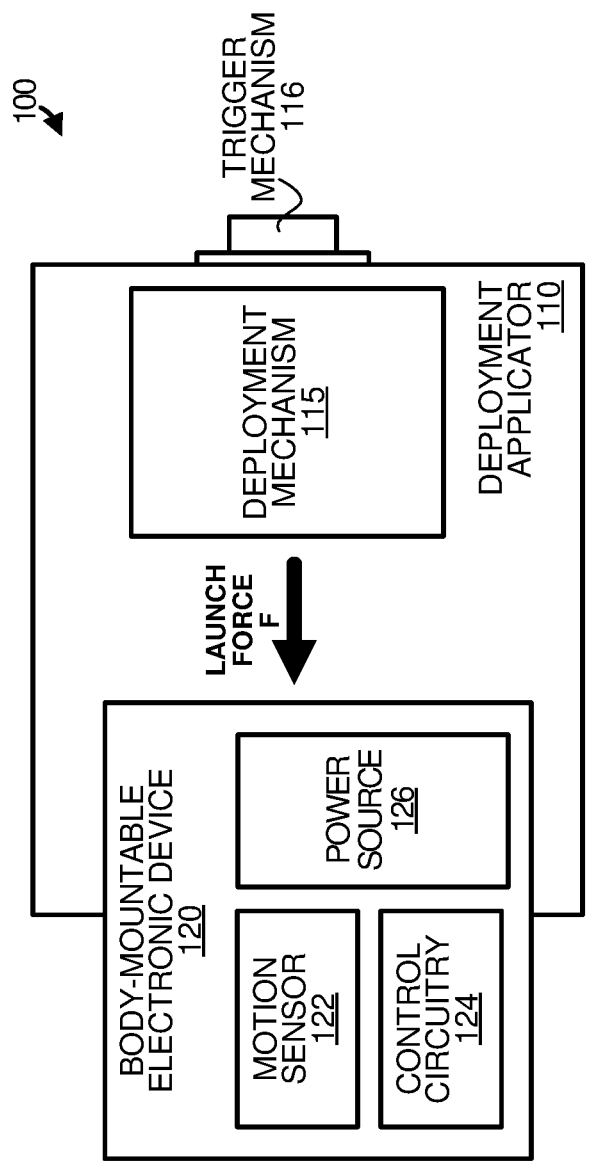
FIG. 1 depicts a block diagram illustrating an example mountable device deployment system including body-mountable electronic device with a two-phase deployment-initiated wakeup mechanism, according to some embodiments.

The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

Examples are discussed in detail below. While specific implementations are discussed, it should be understood that this is done for illustration purposes only. A person skilled in the relevant art will recognize that other components and configurations may be used without parting from the spirit and scope of the subject matter of this disclosure. The implementations may include machine-implemented methods, computing devices, or computer readable medium.

The technology described herein is directed to a two-phase deployment-initiated wakeup mechanism for a body-mountable electronic device. During a first phase of the two-phase wakeup mechanism, a motion sensor detects an acceleration event indicative of deployment of the device onto the body of the user. The acceleration event enables control circuitry thereby transitioning the device from a sleep state to a temporary wakeup verification state. During a second phase of the two-phase mechanism, the control circuitry verifies that the device has been launched onto the body of a user via a deployment applicator in which the device is retained until deployment. Once the control circuitry verifies that the device has been launched onto the body of a user, the control circuitry wakes up the body-mountable electronic device by transitioning the device from the wakeup verification state to a functional (or operational) state. As discussed herein, the term 'body-mountable devices' encompasses implantable medical devices, mountable devices, partially implantable devices, such as continuous glucose monitoring (CGM) devices, and the like, etc.

The wakeup mechanism and techniques discussed herein are implemented using existing components of the body-mountable device, including a motion sensor that is adapted to measure activity of the user during the function (or operational) state. Among other benefits, the wakeup mechanism reduces or eliminates sensor leakage during non-operational time, e.g., transport, storage, etc., and reduces the likelihood of false wakeups while enabling reliable transition from the sleep state to the functional (or operational) state with minimal user interaction.

In some embodiments, the motion sensor comprises an accelerometer that is adapted to detect the high g-force event indicative of deployment of the device onto the body of a user via an applicator. The detection will then wake up a microcontroller (or control circuitry) from an off-state to initiate a second phase of confirmation or verification. During the second phase, the microcontroller attempts to verify that the body-mountable electronic device is deployed by monitoring for and detecting occurrence of a second deployment indicator.

FIG. 1 depicts a block diagram illustrating an example mountable device deployment system 100 including body-mountable electronic device 120 with a two-phase deployment-initiated wakeup mechanism, according to some embodiments. The two-phase deployment-initiated wakeup mechanism is adapted to reliably wake up the body-mountable electronic device 120 responsive to deployment (or launching) of the device onto a body of a user via a deployment applicator 110. As shown in the example of FIG. 1, the device deployment system 100 includes the deployment applicator 110 and the body-mountable electronic device 120 that is inserted or otherwise retained by the deployment applicator 110 prior to deployment.

The deployment applicator 110 can launch or otherwise deploy the body-mountable electronic device 120 onto the body of a user. As shown in the example of FIG. 1, the deployment applicator 110 includes a deployment mechanism 115 and a trigger mechanism 116. Additional or fewer components are possible. The deployment mechanism 115 can include a spring-loaded assembly, a magnetic assembly, or any other apparatus that is able to generate a sufficient launch force F to launch (or deploy) the body-mountable electronic device 120 onto the body of a user.

The trigger mechanism 116 is communicatively and/or mechanically coupled with the deployment mechanism 115 such that activating (or exercising), e.g., pressing, the trigger mechanism 116 causes the deployment mechanism 115 to launch the body-mountable electronic device 120. As shown in the example of FIG. 1, the trigger mechanism 116 comprises a mechanical button or latch mechanism, however, the trigger mechanism 116 can be any mechanical, electrical, etc., mechanism capable of triggering the deployment mechanism 115.

The body-mountable electronic device 120 can be any electronic device that is adapted to monitor and/or sense conditions of the user once the device is deployed onto a body of the user. As shown in the example of FIG. 1, the body-mountable electronic device 120 includes a motion sensor 122, control circuitry 124 and a power source 126. In some embodiments, the motion sensor 122 can be an accelerometer such as, for example, a three-axis digital accelerometer capable of providing a digital output indicating acceleration of the body-mountable electronic device 120.

The control circuitry 124 can include one or more microprocessors, microcontrollers, memories, modules, engines, components, etc., that are configured to verify that the body-mountable electronic device is deployed onto a body of a user during a second phase of the two-phase wakeup mechanism. In some embodiments, the control circuitry 124 generates a second deployment indicator responsive to verification that the body-mountable electronic device has been deployed onto a body of a user via the deployment applicator 110.

The power source 126 can include one or more disposable energy storage devices and any related charging and/or regulator circuitry that provides power to components of the body-mountable electronic device 120. For example, power source 126 can include one or more batteries, capacitors, or other energy storage devices. Although not shown in the example of FIG. 1, the body-mountable electronic device 120 can include one or more additional components such as processors, controllers, memories, etc.

To enhance the longevity of power source 126, the body-mountable electronic device 120 is shipped and stored in a sleep (or pseudo-off) state. As noted above, the body-mountable electronic device 120 includes a two-phase deployment-initiated wakeup mechanism that reliably wakes up the body-mountable electronic device 120 from the sleep (or pseudo-off state) responsive to deployment (or launching) of the device onto a body of a user.

During a first phase of the two-phase wakeup mechanism, motion sensor 122 monitors for the occurrence of a first deployment indictor signifying detection of an acceleration that exceeds a predetermined threshold indicative of deployment of the body-mountable electronic device onto the body of the user. For example, the first deployment indictor can signify detection of a g-force event that exceeds a predetermined threshold g-force value. As discussed herein, the body-mountable electronic device 120 is retained in deployment applicator 110 until the device is deployed.

Responsive to detection of the first deployment indictor, control circuitry 124 is enabled for a second phase of the two-phase wakeup mechanism. During the second phase, the control circuitry attempts to verify that the body-mountable electronic device is deployed onto a body of a user by monitoring for occurrence of a second deployment indicator during a second phase of the two-phase wakeup mechanism.

In some embodiments, the deployment mechanism 115 includes a minimally invasive mechanism for deploying a biosensor in or on the body of the user. For example, the body-mountable electronic device 120 can include an extendable spring-loaded needle adapted to insert the biosensor into the body of the user upon deployment. An example deployment mechanism 115 including the extendable spring-loaded needle is shown and discussed in greater detail with reference to FIGS. 5A-5C. Referring to the second phase of the two-phase wakeup mechanism, in some embodiments, the control circuitry 124 can generate the second deployment indicator when an electrical current measured by the biosensor exceeds a predetermined threshold current value.

As noted above, the body-mountable electronic device 120 can be any electronic device primarily adapted to monitor and/or sense health-related information associated with the user during an operational state. The body-mountable electronic device 120 can provide feedback regarding the health-related information back to the user, e.g., via a built-in interface, via personal communication device, etc.

In some embodiments, the body-mountable electronic device 120 includes a wireless transmitter operably coupled with control circuitry 124 that directs the wireless transmitter to establish a communication channel with the personal communication device. Although not shown in the example of FIG. 1, the personal communication device can be any communication device capable of establishing a wireless connection with the body-mountable electronic device 120 for receiving health-related information. Additionally, the personal communication device can include a display for presenting the health-related information to the user. Example personal communication devices include, but are not limited to, mobile phones, smart watches, etc.

In some embodiments, the control circuitry 124 can monitor the wireless connection and detect the second deployment indicator responsive to successfully establishing a wireless connection between the wireless transmitter and the personal communication device prior to expiry of a timeout period. This process ensures that the user has intentional launched the body-mountable electronic device onto his or her body.

In some embodiments, the control circuitry 124 can be configured to monitor the motion sensor 122 and recognize gestures during the second phase of the two-phase wakeup mechanism. In such instances, the control circuitry 124 can detect the second deployment indicator responsive to detection of a gesture. In some embodiments, a gesture can include a gesture pattern or series of movements. For example, the gesture pattern or series of movements can be a series of taps (on or near the device) by the user or some other movements unlikely to occur by accident.

Figure 2:
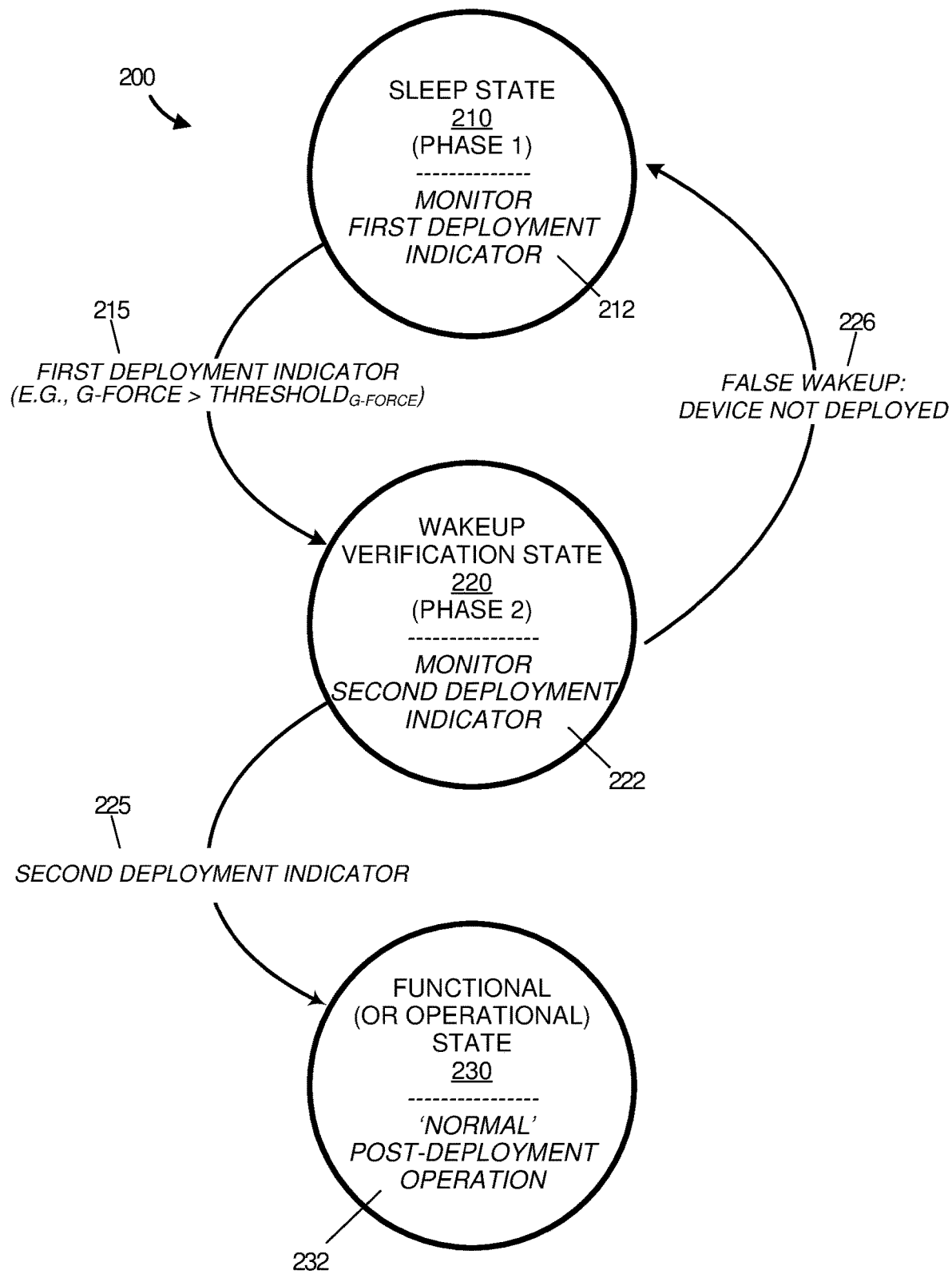
FIG. 2 depicts a state diagram illustrating example operations of a two-phase deployment-initiated wakeup mechanism, according to some embodiments.

FIG. 2 depicts a state diagram 200 illustrating example operations of a two-phase deployment-initiated wakeup mechanism, according to some embodiments. As shown in the example of FIG. 2, the state diagram 200 includes states 210, 220 and 230, entry actions 212, 222 and 232, and transition conditions 215, 225 and 226. The example state operations and transitions shown in state diagram 200 may be performed in various embodiments by a body-mountable electronic device such as, for example, body-mountable electronic device 120 of FIG. 1, or one or more microcontrollers, modules, engines, or components associated therewith. Additional or fewer states, entry actions and transition conditions are possible.

A body-mountable electronic device is placed in sleep state 210 at manufacture time to conserve energy during extended periods of non-operational time, e.g., transport, storage, etc. During a first phase of the two-phase wakeup mechanism, a motion sensor is activated to perform entry action 212. As noted herein, during the sleep state 210, other components of the body-mountable electronic device are disabled. Entry action 212 includes detecting a first deployment indicator. As discussed herein, the first deployment indicator signifies occurrence of an acceleration event indicative of deployment of the body-mountable electronic device via a deployment applicator, e.g., a g-force that exceeds a predetermined g-force threshold.

In the example of FIG. 2, the first deployment indicator acts as transition condition 215 transitioning the body-mountable electronic device from the sleep state 210 to a wakeup verification state 220. Upon entering to the wakeup verification state 220, entry action 222 is performed. As shown in the example of FIG. 2, entry action 222 includes enabling control circuitry for detecting a second deployment indicator to verify the deployment of the body-mountable electronic device via a deployment applicator.

As discussed herein, deployment of the body-mountable electronic device can be verified in a variety of ways. For example, if the body-mountable electronic device is meant to operate while paired to a personal communication device, e.g., mobile phone or smart watch, then a lack of connectivity within a threshold time can indicate a false wakeup. Likewise, if the body-mountable electronic device includes a biosensor, the biosensor readings can be sampled to verify deployment of the sensor and thereby verify deployment of the body-mountable electronic device. For example, if the body-mountable electronic device comprises a continuous glucose monitoring system, an analyte sensor adapted to measure glucose is typically placed beneath the skin. If the sensor is not connected, i.e., the sensor is not in interstitial fluid, then a current flowing through the sensor will be less than a threshold value.

Yet another way deployment of the body-mountable electronic device can be verified is through the use of accelerometer gestures. In some embodiments, verification can be achieved through the detection a gesture or gesture pattern, e.g., three taps and the body-mountable electronic device transitions from the wakeup verification state to an operational state.

While operating in the wakeup verification state 220, the second deployment indicator acts as transition condition 225 transitioning the body-mountable electronic device to an operational state 230 when detected. Upon entering to the operational state 230, entry action 232 enables a normal operation of the body-mountable electronic device. As discussed herein, during the operational state 230, the body-mountable electronic device 120 is adapted to perform its primary functions, e.g., monitoring and/or sensing health-related information associated with the user on which the device is deployed and providing feedback regarding the health-related information. It is appreciated that primary functionality is disabled during sleep state 210 and wakeup verification state 220.

Figure 3A:
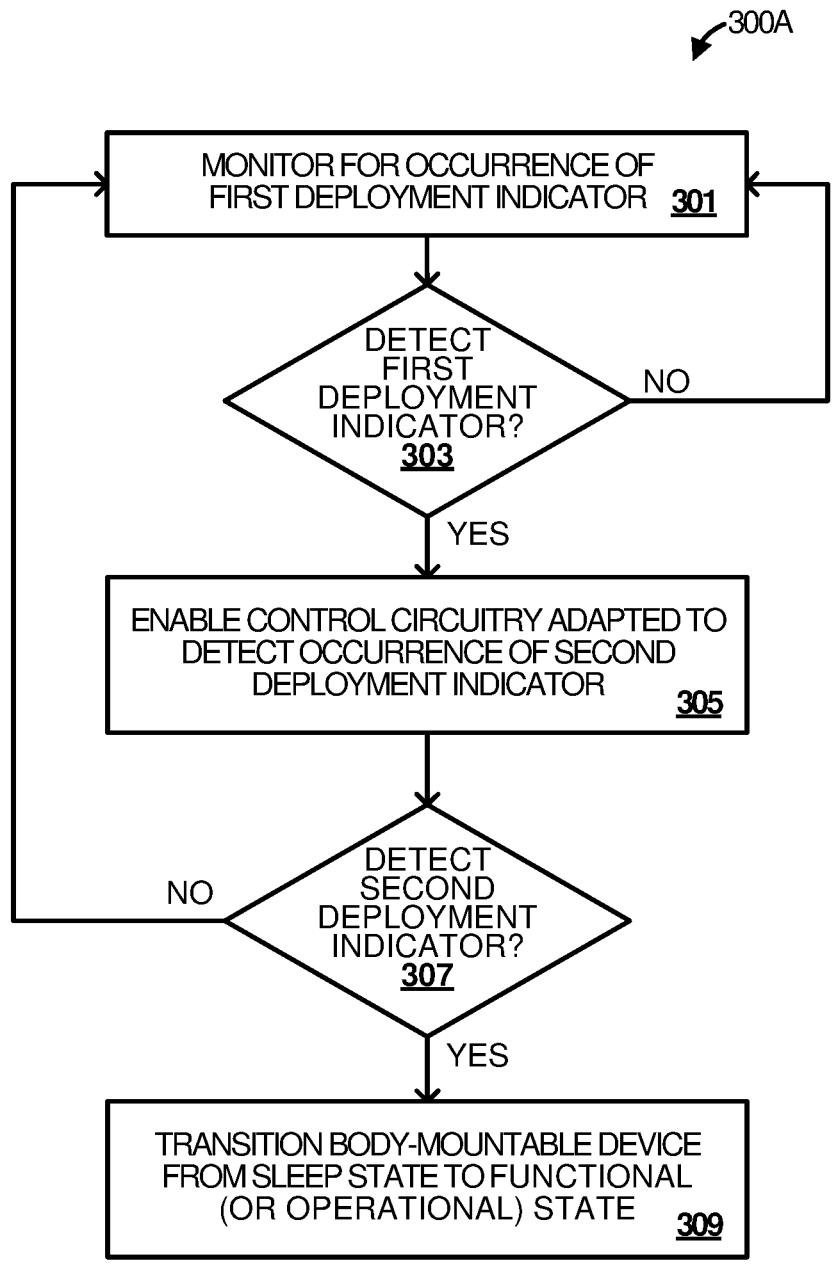
FIGS. 3A and 3B depict flow diagrams illustrating example operations for reliably transitioning a body-mountable electronic device from a sleep state to a functional (or operational) state responsive to deployment of the mountable device by a deployment applicator onto the body of a user, according to some embodiments.
Figure 3B:
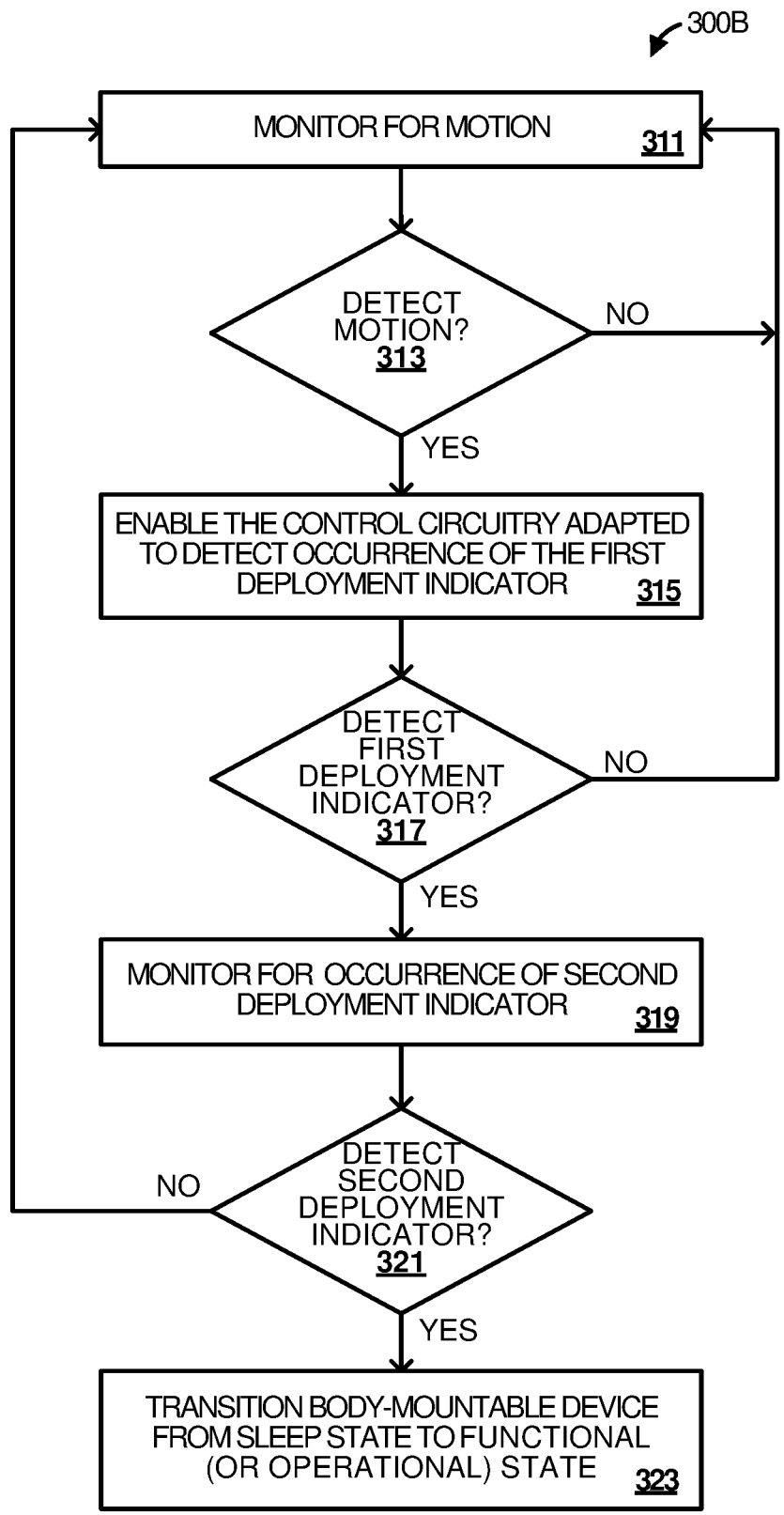

FIGS. 3A and 3B depict flow diagrams illustrating example operations 300A and 300B, respectively, for reliably transitioning a body-mountable electronic device from a sleep state to a functional (or operational) state responsive to deployment of the mountable device by a deployment applicator onto the body of a user, according to some embodiments. More specifically, the example operations 300A depict an implementation whereby the motion sensor detects a first deployment indicator and example operations 300B depict an implementation whereby control circuitry detects the first deployment indicator. The example operations 300A and 300B may be performed in various embodiments by a body-mountable electronic device such as, for example, body-mountable electronic device 120 of FIG. 1, or one or more microcontrollers, modules, engines, or components associated therewith. Additional or fewer states, entry actions and transition conditions are possible.

Referring first to the example of FIG. 3A, to begin, at 301, during a first phase of the two-phase wakeup mechanism, a motion sensor of the body-mountable electronic device monitors for occurrence of a first deployment indicator while in a sleep state. As discussed herein, the first deployment indicator signifies an acceleration event indicative of deployment of the body-mountable electronic device onto the body of the user. At decision 303, the body-mountable electronic device determines if the first deployment indicator is detected. If the first deployment indicator is not detected, the motion sensor continues to monitor, at 301, for occurrence of the first deployment indicator.

However, if the first deployment indicator is detected, at 305, control circuitry of the body-mountable electronic device is enabled thereby transitioning the body-mountable electronic device from a sleep state to a wakeup verification state for a second phase of the two-phase wakeup mechanism. At decision 307, the body-mountable electronic device determines if the second deployment indicator is detected. If the second deployment indicator is not detected, the body-mountable electronic device returns to the sleep state and the motion sensor continues to monitor, at 301, for occurrence of the first deployment indicator. However, if the second deployment indicator is detected, at 309, control circuitry transitions the body-mountable electronic device from the wakeup verification state to an operational state.

The examples discussed herein primarily include a motion sensor that is adapted to detect the first deployment indicator, e.g., a g-force that exceeds a predetermined threshold. However, in some implementations, the control circuitry can be enabled by any motion and the control circuitry can be adapted to detect the first deployment indicator, e.g., motion exceeding a threshold. The example of FIG. 3B illustrates this implementation and discusses the operation in greater detail.

Referring next to the example of FIG. 3B, to begin, at 311, during a first phase of the two-phase wakeup mechanism, a motion sensor of the body-mountable electronic device monitors for motion while the device is in a sleep state (e.g., control circuitry or microcontroller in sleep state). At decision 313, the motion sensor determines if motion is detected. If motion is detected, at 315, control circuitry of the body-mountable electronic device is enabled thereby transitioning the body-mountable electronic device from a sleep state to a wakeup verification state for a second phase of the two-phase wakeup mechanism.

At decision 317, the control circuitry of the body-mountable electronic device determines if the first deployment indicator is detected. As discussed herein, the first deployment indicator signifies an acceleration event indicative of deployment of the body-mountable electronic device onto the body of the user. If the first deployment indicator is not detected, the body-mountable electronic device returns to the sleep state and the motion sensor continues to monitor, at 311, for occurrence of motion. However, if the first deployment indicator is detected, at 319, the control circuitry of the body-mountable electronic device monitors for occurrence of the second deployment indicator. At decision 321, the body-mountable electronic device determines if the second deployment indicator is detected. If the second deployment indicator is not detected, then the motion sensor continues to monitor, at 311, for occurrence of motion. However, if the second deployment indicator is detected, at 309, the control circuitry transitions the body-mountable electronic device from the wakeup verification state to an operational state.

Figure 4:
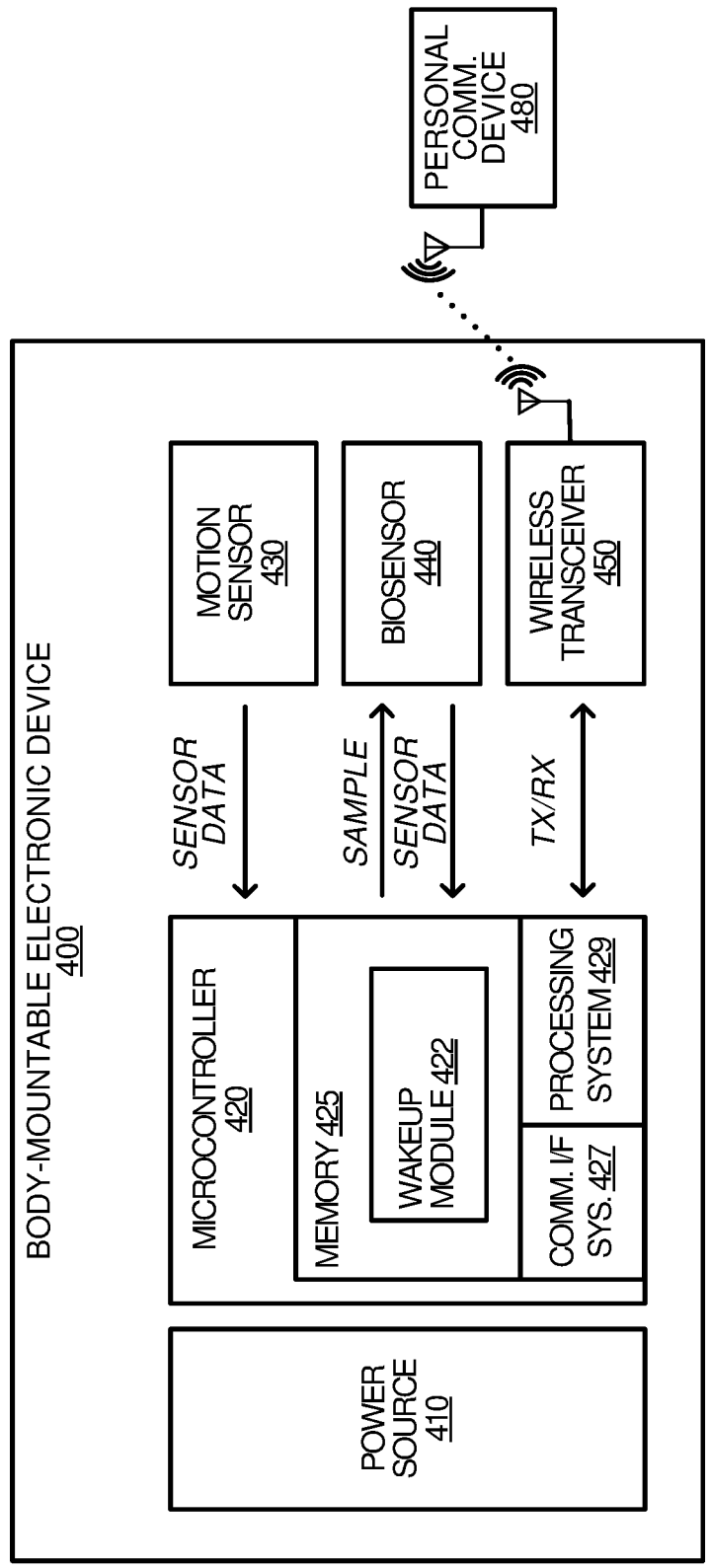
FIG. 4 depicts example components of a body-mountable electronic device including a two-phase deployment-initiated wakeup mechanism, according to some embodiments.

FIG. 4 depicts example components of a body-mountable electronic device 400 including a two-phase deployment-initiated wakeup mechanism, according to some embodiments. The body-mountable electronic device can be body-mountable electronic device 120 of FIG. 1, although alternative configurations are possible. As illustrated in the example of FIG. 4, example components 400 include power source 410, microcontroller 420, motion sensor 430, biosensor 440, and wireless transceiver 450. Additional or fewer components are possible.

Power source 410 provides power to the other example components 400. The power source 410 can include one or more energy storage devices and any related charging and/or regulator circuitry. In some embodiments, power source 410 can include one or more disposable batteries, capacitors, or other energy storage devices.

The microcontroller 420 can be a small computer or other circuitry that retrieves and executes software from memory 425. The microcontroller 420 may be implemented within a single device or system on a chip (SoC) or may be distributed across multiple processing devices that cooperate in executing program instructions. As shown in the example of FIG. 4, the microcontroller 420 includes memory 425, a communication interface 427, and a processing system 429. The microcontroller 420 is operatively or communicatively coupled with various sensors including the motion sensor 430 and the biosensor 440. Additionally, as shown in the example of FIG. 4, the microcontroller 420 is operatively or communicatively coupled with the wireless transceiver 450.

The memory 425 can include program memory and data memory. As shown, memory 425 includes a wakeup module 422. Other modules are also possible. Although shown as software modules in the example of FIG. 4, functionality of wakeup module 422 can be implemented individually or in any combination thereof, partially or wholly, in hardware, software, or a combination of hardware and software.

The communication interface 427 may include communication connections and devices that together facilitate communication with auxiliary (or personal communication) devices such as, for example, mobile phones or smart watches, as well as other electronic devices via at least wireless transceiver 450. The processing system 429 can include one or more processor cores that are configured to retrieve and execute the wakeup module 422 for reliably assisting in performing the two-phase wakeup mechanism as discussed herein.

The motion sensor 430 senses motion of the body-mountable electronic device. The motion sensor can be, for example, a three-axis digital accelerometer that provides a digital output indicating acceleration of the body-mountable electronic device to the microcontroller 420.

The biosensor 440 detects an analyte or interstitial fluid. In some embodiments, biosensor 440 can be a hair-like sensor that is positioned just beneath the surface of the skin of a user upon deployment. In some embodiments, the biosensor 440 provides the microcontroller 420 with raw values of the readings.

The wireless transceiver 450 can be, for example, a Bluetooth™ or Bluetooth Low Energy™ (BLE) transceiver. Other wireless transceiver technologies, including Wi-Fi™ and Infrared technologies are also possible. In some embodiments, the body-mountable electronic device 400 is adapted to pair with a personal communication device 480, e.g., a smart phone or watch. As discussed herein, the pairing process can be monitored and used as a second phase of the two-phase wakeup mechanism. For example, if there is no Bluetooth Low Energy (BLE) connection within a predetermined timeout period, e.g., ten minutes, then the system times out.

Referring to the wakeup module 422, in operation, the module can direct the microcontroller 420 to perform one or more operations to verify deployment of a body-mountable electronic device 400 responsive to detection of acceleration event indicative of the deployment of the body-mountable electronic device. Performing the operations can result in a determination that the acceleration event was a false wakeup, e.g., not a deployment onto a body of a user via the deployment applicator. In such instances, the microcontroller 420 directs the body-mountable electronic device to return or remain in a sleep state. Alternatively, if the operations result in a determination that the body-mountable electronic device was deployed onto the body of a user via the deployment applicator, then the body-mountable electronic device transitions to an operational state.

As discussed herein, during the operational state, the body-mountable electronic device 400 performs its primary functions, e.g., monitors and/or senses health-related information associated with the user.

Figure 5A:
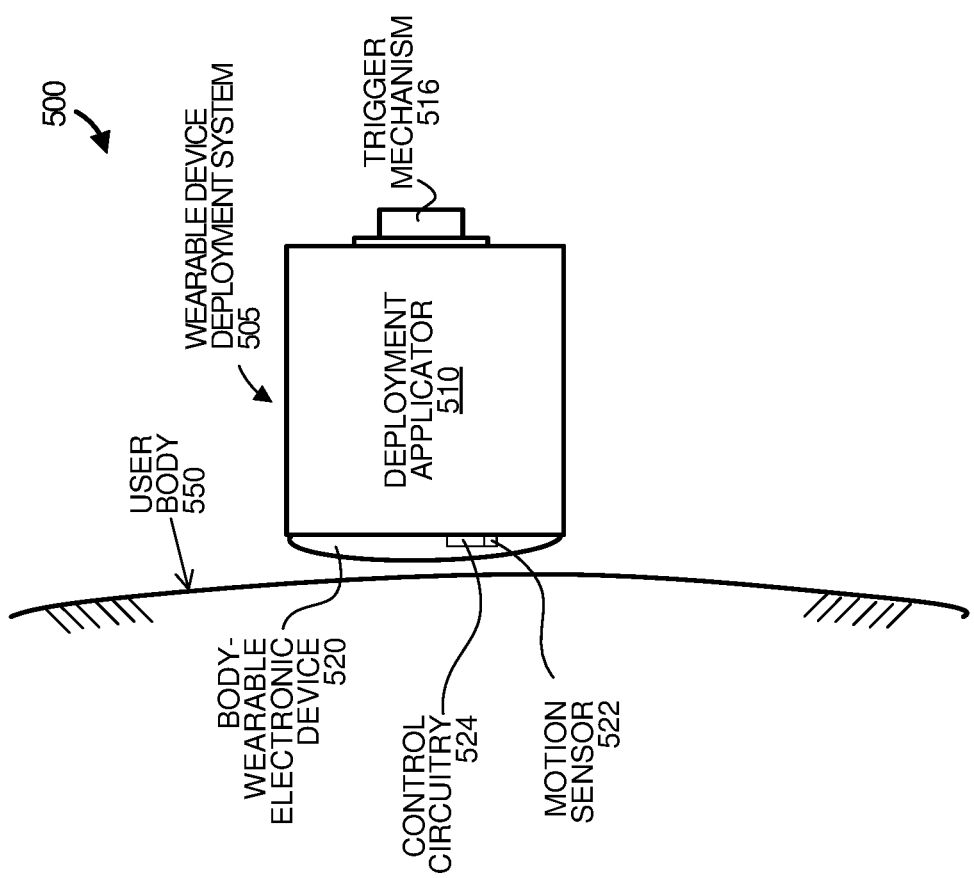
Figure 5B:
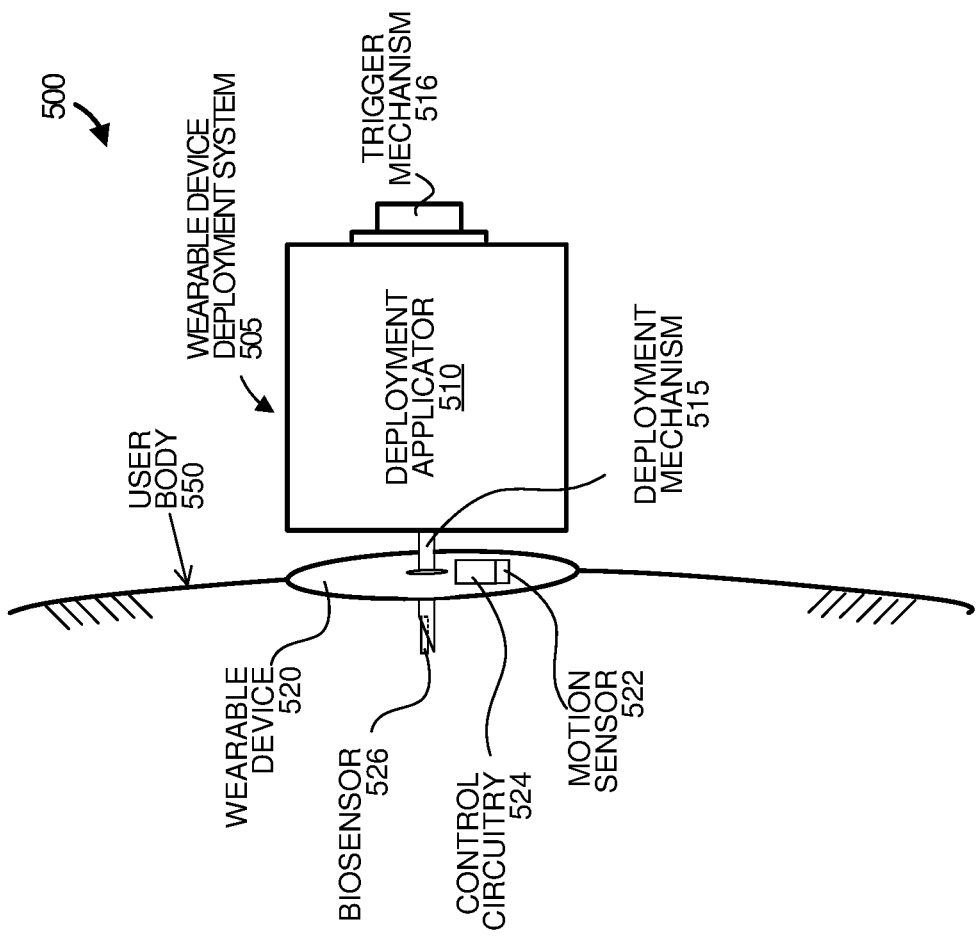

FIGS. 5A-5C depict diagrams illustrating an example operational environment 500 during various stages of deploying a body-mountable electronic device 520 retained in a mountable device deployment system 505 onto a user body 550, according to some embodiments. More specifically, the examples of FIGS. 5A, 5B and 5C illustrate the example deployment environment 500 prior to deployment of the body-mountable electronic device 520 on the user body 550, during deployment of the body-mountable electronic device 520 on the user body 550, and after deployment of the body-mountable electronic device 520 on the user body 550, respectively.

As shown in the examples of FIGS. 5A-5C, the example operational environment 500 includes a mountable device deployment system 505 and user body 550. The mountable device deployment system 505 includes a deployment applicator 510 and the body-mountable electronic device 520. The deployment applicator 510 can launch or otherwise deploy the body-mountable electronic device 520 onto the user body 550. The body-mountable electronic device 520 can include a base having a bio-compatible adhesive disposed on a proximal surface for removably attaching the body-mountable electronic device to skin of the user.

The deployment applicator 510 includes a deployment mechanism 515 and a trigger mechanism 516. As shown in the examples of FIGS. 5B and 5C, the deployment mechanism 515 is in the form of an extendable spring-loaded needle that is adapted to insert a hair-like biosensor 526 just beneath the surface of the user body 550 upon deployment. The trigger mechanism 516 is communicatively and/or mechanically coupled with the deployment mechanism 515 such that exercising, e.g., pressing, the trigger mechanism 516 causes the deployment mechanism 515 to launch the body-mountable electronic device 520. As shown in the example of FIGS. 5A-5C, the trigger mechanism 516 comprises a mechanical button or latch mechanism, however, the trigger mechanism 516 can be any mechanical, electrical, etc., mechanism capable of triggering the deployment mechanism 515.

The body-mountable electronic device 520 can be any electronic device that is adapted to monitor and/or sense conditions of the user once the device is deployed onto a body of the user. In some embodiments, the body-mountable electronic device 520 can be a body-mountable electronic device 120 of FIG. 1, although alternative configurations are possible.

As shown in the example of FIGS. 5A-5C, the body-mountable electronic device 520 includes a motion sensor 522, control circuitry 524 and a power source (not shown). In some embodiments, the motion sensor 522 can be an accelerometer capable of providing an output indicating accelerations detected by the body-mountable electronic device 520.

Referring first to FIG. 5A, FIG. 5A illustrates a first phase of the two-phase wakeup mechanism as motion sensor 522 monitors for the occurrence of a first deployment indictor signifying detection of an acceleration event that exceeds a predetermined threshold indicative of deployment of the body-mountable electronic device 520 onto the user body 550.

As shown in the example of FIG. 5B, responsive to detection of the first deployment indictor, control circuitry 524 is enabled for a second phase of the two-phase wakeup mechanism. During the second phase, the control circuitry 524 attempts to verify that the body-mountable electronic device is deployed onto the user body 550 by monitoring for occurrence of a second deployment indicator during the second phase.

As shown in the example of FIG. 5C, during the second phase of the two-phase wakeup mechanism, the control circuitry 524 generates the second deployment indicator when an electrical current measured by the biosensor 526 exceeds a predetermined threshold current value. As discussed herein, the body-mountable electronic device 520 can be any electronic device primarily adapted to monitor and/or sense health-related information associated with the user during an operational state. Once deployed, the body-mountable electronic device 520 can provide feedback regarding the health-related information back to the user, e.g., via a built-in interface, via personal communication device, etc. The feedback can provide useful real-time or near real-time health-related information to a user. For example, glucose levels and information on how the glucose levels are affected by food, activities, etc., can be provided to a user with type I, II or prediabetes.

Figure 6:
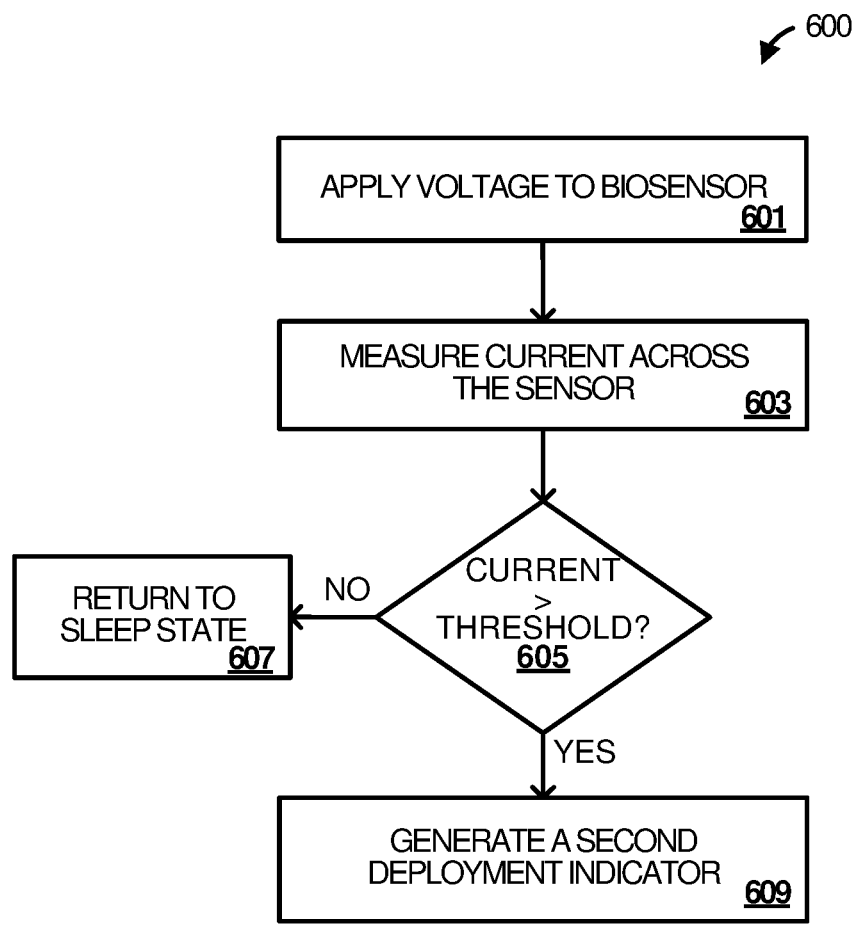
FIG. 6 depicts a flow diagram illustrating example operations for verifying deployment of a body-mountable electronic device using a biosensor adapted to detect an analyte or interstitial fluid, according to some embodiments.
Figure 7:
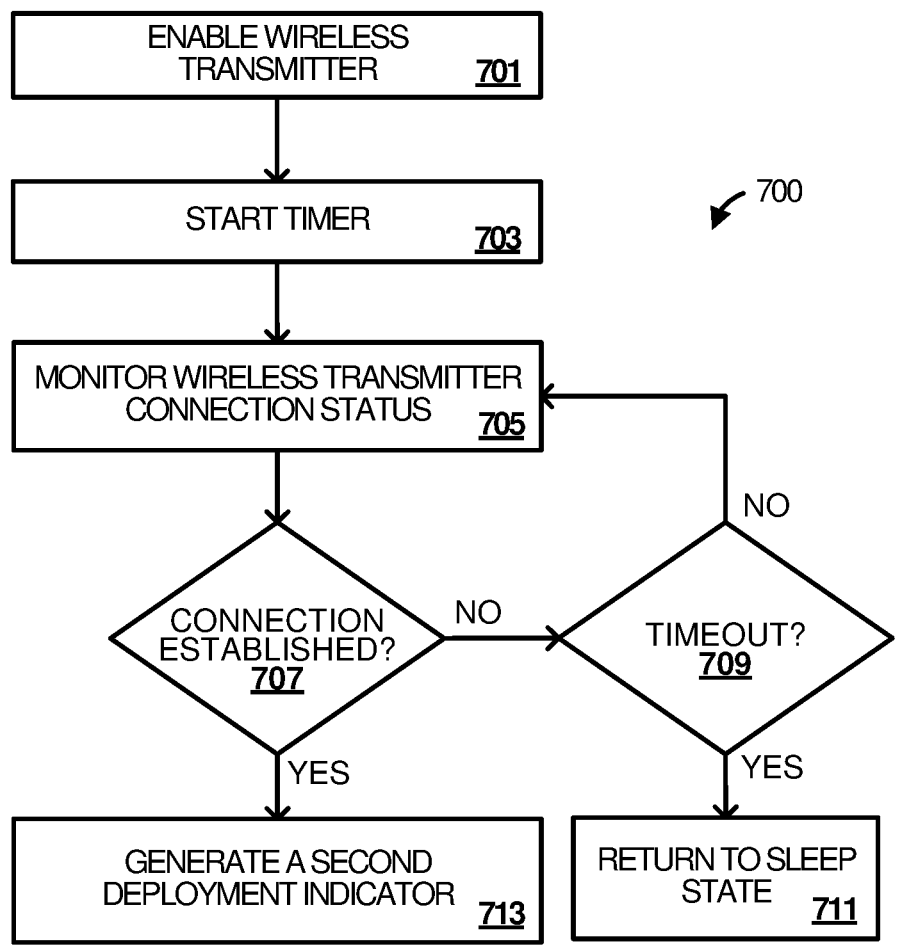
FIG. 7 depicts a flow diagram illustrating example operations for verifying deployment of a body-mountable electronic device using a wireless transmitter adapted to establish a wireless connection with a personal communication device, according to some embodiments.
Figure 8:
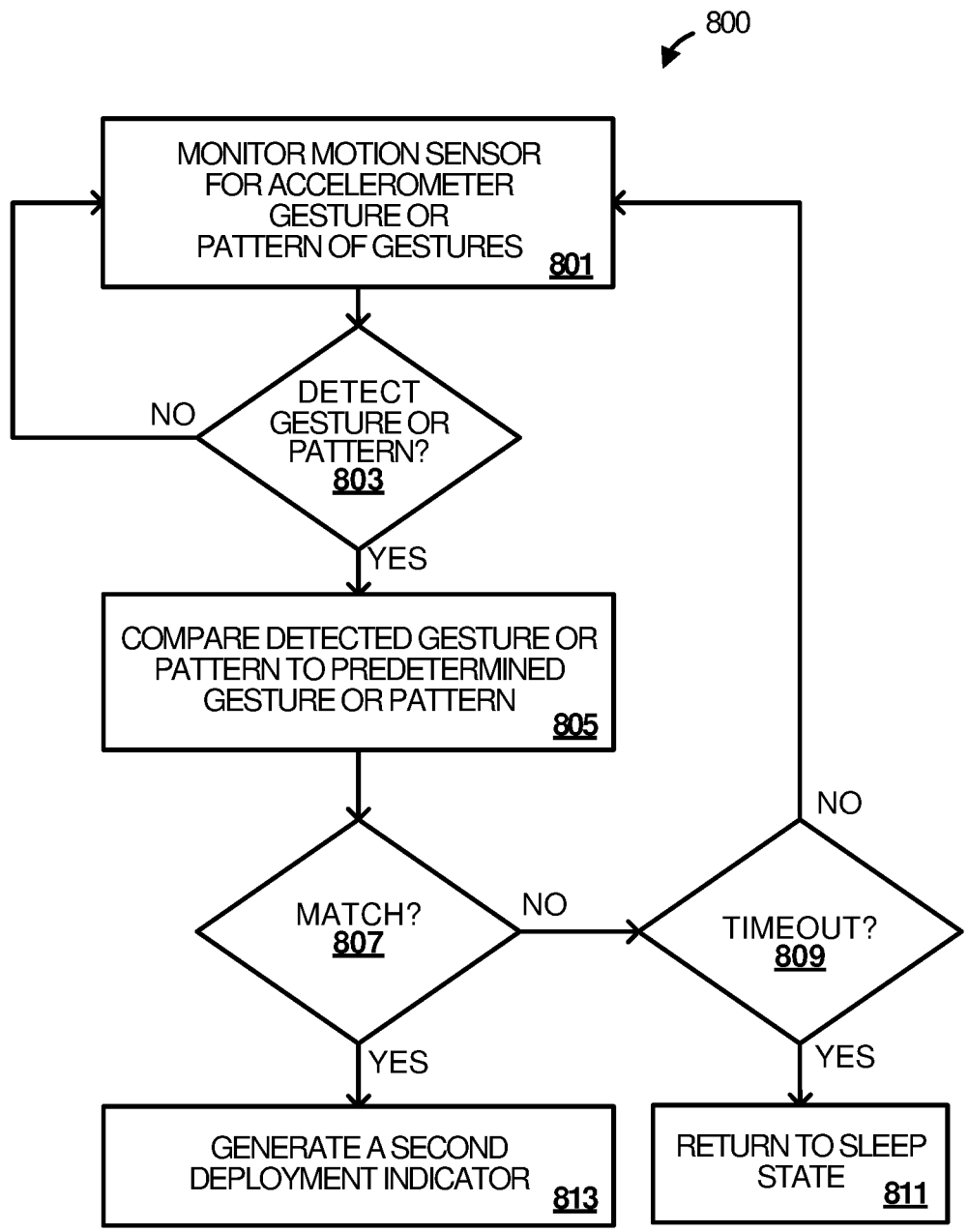
FIG. 8 depicts a flow diagram illustrating example operations for verifying deployment of a body-mountable electronic device via one or more accelerometer gestures, according to some embodiments.

FIGS. 6-8 depict flow diagrams illustrating example operations performed during a second phase of a two-phase wakeup mechanism, according to some embodiments. The example operations discussed with reference to FIGS. 6-8 may be performed in various embodiments by a body-mountable electronic device such as, for example, body-mountable electronic device 120 of FIG. 1, or one or more microcontrollers, modules, engines, or components associated therewith.

As discussed herein, the body-mountable electronic device is shipped and stored in a sleep (or pseudo-off) state. The body-mountable electronic device includes a two-phase deployment-initiated wakeup mechanism that reliably wakes up the body-mountable electronic device from the sleep (or pseudo-off) state to a functional (or operational) state responsive to deployment (or launching) of the device onto a user body. During a first phase of the two-phase wakeup mechanism, a motion sensor detects an acceleration event indicative of deployment of the device onto the body of the user. During a second phase of the two-phase mechanism, control circuitry is enabled to verify that the device has been launched onto the body of a user and, thus, reduce a likelihood of a false wakeup, e.g., unintended transitions to the functional (or operational) state.

Referring first to the example of FIG. 6, FIG. 6 depicts a flow diagram illustrating example operations 600 for verifying deployment of a body-mountable electronic device using a biosensor adapted to detect an analyte or interstitial fluid, according to some embodiments.

To begin, at 601, the body-mountable electronic device applies a voltage to the biosensor and, at 603, measures the current across the biosensor. As discussed herein, if the biosensor (analyte) sensor is deployed, i.e., the sensor is in interstitial fluid, then a current will be flowing through the device. Likewise, if the biosensor (analyte) sensor is not deployed, i.e., the sensor is not in interstitial fluid, then a current should not be flowing through the device.

At decision 605, the body-mountable electronic device determines if the measured current exceeds a predetermined current threshold. It is appreciated that in humid environments, it is possible to detect a small current flow even when the biosensor is not deployed. Accordingly, the predetermined current threshold can be set to a nominal value to reduce false wakeups in humid environments. If the measured current does not exceed the predetermined current threshold, the body-mountable electronic device remains or returns to the sleep state. However, if the measured current does exceed the predetermined current threshold, at 609, the body-mountable electronic device generates the second deployment indicator.

FIG. 7 depicts a flow diagram illustrating example operations 700 for verifying deployment of a body-mountable electronic device using a wireless transmitter adapted to establish a wireless connection with a personal communication device, according to some embodiments.

To begin, at 701, the body-mountable electronic device enables the wireless transmitter. For example, the body-mountable electronic device can enable a BLE transceiver of the body-mountable electronic device. Once enabled, the device is discoverable and can be paired with a personal communication device such as, for example, personal electronic device 480 of FIG. 4. At 703, the body-mountable electronic device starts a timer. The timer can count up or down, but a wireless connection must be established within a predetermined timeout or period.

At 705, the body-mountable electronic device monitors a connection status of the wireless transmitter and, at decision 707, determines if a connection has been established, e.g., if the body-mountable electronic device and the personal communication device have paired. If a connection has not been established, at decision 709, the body-mountable electronic device determines if the timeout period has occurred. For example, if there is no BLE connection within a predetermined timeout period, e.g., ten minutes, then the system times out and, at 711, returns to a sleep (or pseudo-off) state. Returning to decision 707, if a connection is established, at 713, the body-mountable electronic device generates the second deployment indicator which, in the example of FIG. 7, is indicative of establishment of a wireless connection between the wireless transmitter and the personal communication device prior to expiry of the timeout period.

FIG. 8 depicts a flow diagram illustrating example operations 800 for verifying deployment of a body-mountable electronic device via one or more accelerometer gestures, according to some embodiments.

To begin, at 801, the body-mountable electronic device monitors the motion sensor for detection of an accelerometer gesture or pattern of gestures. At decision 803, the body-mountable electronic device determines if the accelerometer gesture or pattern of gestures is detected. If not, the body-mountable electronic device continues monitoring the motion sensor at step 801. Otherwise, at 805, the body-mountable electronic device compares the detected gesture or pattern of gestures to a predetermined gesture or pattern. For example, a pattern of gestures can include a series of movements or taps. At decision 807, the body-mountable electronic device determines if there is a match. If there is not a match, at decision 809, the body-mountable electronic device determines if a timeout period has occurred. If the timeout period has occurred, at 811, the body-mountable electronic device returns to a sleep (or pseudo-off) state. Otherwise, the body-mountable electronic device continues to monitor for gestures at 801. Returning to decision 807, if the gesture or pattern of gestures match a predetermined gesture or pattern, at 813, the body-mountable electronic device generates the second deployment indicator.

Certain inventive aspects may be appreciated from the foregoing disclosure, of which the following are various examples.

Example 1. A mountable device deployment system comprising: a body-mountable electronic device including: a motion sensor adapted to detect a first deployment indicator, the first deployment indicator comprising an acceleration event indicative of deployment of the body-mountable electronic device, and control circuitry adapted to transition the body-mountable electronic device from a sleep state to a wakeup verification state responsive to the first deployment indicator, and to transition the body-mountable electronic device from the wakeup verification state to an operational state responsive to detecting a second deployment indicator; and a deployment applicator having the body-mountable electronic device retained therein, the deployment applicator including a deployment mechanism adapted to launch the body-mountable electronic device.

Example 2. The system of Example 1, wherein the body-mountable electronic device further includes a biosensor adapted to detect an analyte or interstitial fluid.

Example 3. The system of Example 2, wherein the deployment mechanism comprises an extendable spring-loaded needle adapted to insert the biosensor into a body of a user upon deployment, and wherein the acceleration event is indicative of the launching of the extendable spring-loaded needle.

Example 4. The system of Example 3, wherein the deployment applicator is adapted to retain the body-mountable electronic device until the extendable spring-loaded needle retracts and thereby disposing the body-mountable electronic device on the body of the user and the biosensor beneath a surface of skin of the user.

Example 5. The system of Example 3, wherein the body-mountable electronic device further includes: a base having a bio-compatible adhesive disposed on a proximal surface for attaching the body-mountable electronic device to skin of the user.

Example 6. The system of Example 2, wherein the control circuitry is further adapted to detect the second deployment indicator when an electrical current measured by the biosensor matches a preset pattern.

Example 7. The system of Example 6, wherein the electrical current measured by the biosensor matches the preset pattern when the electrical current exceeds a predetermined threshold value.

Example 8. The system of Example 1, wherein the body-mountable electronic device further includes: a wireless transmitter operably coupled with the control circuitry and adapted to transmit information to a communication device, wherein the control circuitry is further adapted to detect the second deployment indicator responsive to establishment of a wireless connection between the wireless transmitter and the communication device prior to expiry of a timeout.

Example 9. The system of Example 1, wherein the control circuitry is further adapted to detect the second deployment indicator responsive to detecting a gesture pattern in motion signals outputted by the motion sensor.

Example 10. The system of Example 9, wherein the gesture pattern comprises a pattern of body mountable electronic device movements, a pattern of rotations, a pattern of taps, or a combination thereof.

Example 11. The system of Example 1, wherein detecting the acceleration event includes detecting a g-force that exceeds a predetermined g-force threshold.

Example 12. The system of Example 1, wherein the deployment applicator further comprises: a triggering mechanism mechanically coupled with the deployment mechanism and adapted to direct the deployment mechanism to launch the body-mountable electronic device responsive to activation.

Example 13. A body-mountable electronic device comprising: a motion sensor adapted to detect, during a first phase of a two-phase wakeup mechanism while the body-mountable electronic device is in a sleep state, a first deployment indicator comprising an acceleration event indicative of deployment of the body-mountable electronic device; and a microcontroller enabled by the acceleration event and adapted to: transition the body-mountable electronic device from the sleep state to a wakeup verification state; verify that the body-mountable electronic device is deployed onto a body of a user during a second phase of the two-phase wakeup mechanism, wherein the microcontroller detects a second deployment indicator responsive to a verification that the body-mountable electronic device is deployed; and transition the body-mountable electronic device from the wakeup verification state to an operational state responsive to detecting the second deployment indicator.

Example 14. The body-mountable electronic device of claim 13, further comprising: a biosensor operably coupled with the microcontroller and adapted to detect an analyte or interstitial fluid, wherein the microcontroller detects the second deployment indicator when an electrical current measured across the biosensor exceeds a predetermined threshold value.

Example 15. The body-mountable electronic device of claim 13, further comprising: a wireless transmitter operably coupled with the microcontroller and adapted to transmit information to a communication device, wherein the microcontroller is further adapted to detect the second deployment indicator responsive to establishment of a wireless connection between the wireless transmitter and the communication device prior to expiry of a timeout.

Example 16. The body-mountable electronic device of claim 13, wherein the microcontroller is further adapted to detect the second deployment indicator responsive to detecting a gesture pattern in motion signals outputted by the motion sensor.

Example 17. The body-mountable electronic device of claim 13, wherein the acceleration event includes detecting a g-force that exceeds a predetermined g-force threshold.

Example 18. A method of waking up a body-mountable electronic device, the method comprising: monitoring for occurrence of a first deployment indicator while in a sleep state, wherein the first deployment indicator comprising an acceleration event indicative of deployment of the body-mountable electronic device onto a body of a user; responsive to detecting the first deployment indicator, enabling control circuitry adapted to detect occurrence of a second deployment indicator, wherein enabling the control circuitry transitions the body-mountable electronic device from the sleep state to a wakeup verification state; and responsive to detecting the second deployment indicator, transitioning the body-mountable electronic device from the wakeup verification state to an operational state.

Example 19. The method of claim 18, wherein to detect the occurrence of the second deployment indicator, the control circuitry is further adapted to: apply a voltage to a biosensor, wherein the biosensor is adapted to detect an analyte or interstitial fluid; measure a current across the biosensor; determine if the current across the biosensor exceeds a predetermined threshold; and detect the second deployment indicator responsive to the current across the biosensor exceeding the predetermined threshold.

Example 20. The method of claim 18, wherein to detect the occurrence of the second deployment indicator, the control circuitry is further adapted to: monitor a connection status of a wireless transmitter of the body-mountable electronic device; and detect the second deployment indicator responsive to detecting a wireless connection between the wireless transmitter and a communication device prior to expiry of a timeout.

Example 21. The method of claim 18, wherein to detect the occurrence of the second deployment indicator, the control circuitry is further adapted to: monitor the motion sensor for occurrence of a gesture pattern in motion signals outputted by the motion sensor; and detect the second deployment indicator responsive to detecting the gesture pattern in the motion signals outputted by the motion sensor.

Example 22. A mountable device deployment system comprising: a body-mountable electronic device including: a motion sensor adapted to detect motion, and control circuitry adapted to enable responsive to detecting the motion and, once enabled, determine if the motion comprises an acceleration event indicative of deployment of the body-mountable electronic device, and when the acceleration event is indicative of deployment of the body-mountable electronic device, transition the body-mountable electronic device to an operational state responsive to detecting a second deployment indicator; and a deployment applicator having the body-mountable electronic device retained therein, the deployment applicator including a deployment mechanism adapted to launch the body-mountable electronic device.

The functional block diagrams, operational scenarios and sequences, and flow diagrams provided in the Figures are representative of exemplary systems, environments, and methodologies for performing novel aspects of the disclosure. While, for purposes of simplicity of explanation, methods included herein may be in the form of a functional diagram, operational scenario or sequence, or flow diagram, and may be described as a series of acts, it is to be understood and appreciated that the methods are not limited by the order of acts, as some acts may, in accordance therewith, occur in a different order and/or concurrently with other acts from that shown and described herein. For example, those skilled in the art will understand and appreciate that a method could alternatively be represented as a series of interrelated states or events, such as in a state diagram. Moreover, not all acts illustrated in a methodology may be required for a novel implementation.

The descriptions and figures included herein depict specific implementations to teach those skilled in the art how to make and use the best option. For the purpose of teaching inventive principles, some conventional aspects have been simplified or omitted. Those skilled in the art will appreciate variations from these implementations that fall within the scope of the invention. Those skilled in the art will also appreciate that the features described above can be combined in various ways to form multiple implementations. As a result, the invention is not limited to the specific implementations described above, but only by the claims and their equivalents.

What is claimed is:

1. A method, comprising:
    detecting, by a body-mountable electronic device in a low-power mode, a first initial deployment indicator;
    in response to detecting the first initial deployment indicator, transitioning the body-mountable electronic device from the low-power mode into a mid-power mode;
    failing to verify, by the body-mountable electronic device in the mid-power mode, deployment of the body-mountable electronic device within a threshold time period;
    in response to the failing, transitioning the body-mountable electronic device from the mid-power mode into the low-power mode;
    detecting, by the body-mountable electronic device in the low-power mode, a second initial deployment indicator after the first initial deployment indicator;
    in response to detecting the second initial deployment indicator, transitioning the body-mountable electronic device from the low-power mode into the mid-power mode;
    verifying, by the body-mountable electronic device in the mid-power mode, deployment of the body-mountable electronic device based on detecting a signal within the threshold time period; and
    in response to the verifying, transitioning the body-mountable electronic device from the mid-power mode into a full power mode.

2. The method of claim 1, wherein the detecting the signal comprises:
    detecting connectivity between the body-mountable electronic device and a mobile device within the threshold time period.

3. The method of claim 1, wherein the detecting the signal comprises:
    detecting biosensor readings from a biosensor of the body-mountable electronic device within the threshold time period.

4. The method of claim 1, wherein the detecting the signal comprises:
    detecting an analyte from an analyte sensor of the body-mountable electronic device within the threshold time period.

5. The method of claim 1, wherein the detecting the signal comprises:
    detecting a pattern of movements of the body-mountable electronic device within the threshold time period.

6. The method of claim 1, wherein:
    the transitioning the body-mountable electronic device from the low-power mode to the mid-power mode comprises enabling control circuitry; and
    the control circuitry performs the verifying.

7. The method of claim 1, wherein:
    the body-mountable electronic device comprises a sensor component, a microcontroller, and a plurality of other components;
    the sensor component is enabled, the microcontroller is disabled, and the plurality of other components are disabled in the low-power mode;
    the transitioning the body-mountable electronic device from the low-power mode to the mid-power mode comprises enabling the microcontroller; and
    the transitioning the body-mountable electronic device from the mid-power mode to the full power mode comprises enabling the plurality of other components.

8. The method of claim 1, wherein the detecting the initial deployment indicator comprises detecting an acceleration event.

9. The method of claim 1, further comprising:
    detecting, by the body-mountable electronic device in the low-power mode, a plurality of initial deployment indicators prior to detecting the first initial deployment indicator; and
    in response to detecting each of the plurality of initial deployment indicators:
        transitioning the body-mountable electronic device from the low-power mode into the mid-power mode;
        failing to verify, by the body-mountable electronic device in the mid-power mode, deployment of the body-mountable electronic device within the threshold time period; and
        in response to the failing, transitioning the body-mountable electronic device from the mid-power mode into the low-power mode.

10. The method of claim 1, further comprising:
    providing, by the body-mountable electronic device in the full power mode, health related information associated with a user on which the body-mountable electronic device is mounted.

11. A body-mountable electronic device, comprising:
    a power source;
    a timer configured to count a timeout period;
    a sensor coupled to the power source and configured to detect an indication that meets a transition condition; and
    control circuitry coupled to the power source and configured to:
        verify deployment of the body-mountable electronic device upon being enabled in response to the transition condition being met, wherein:
            upon being enabled, the control circuitry draws a first level of power from the power source; and
            verifying the deployment is based on the control circuitry monitoring to detect a signal within the timeout period, and
        in response to verifying the deployment, transition the body-mountable electronic device to a full power mode, wherein the transitioning comprises enabling additional functionality of the body-mountable electronic device, and wherein enabling the additional functionality draws a second level of power from the power source,
    wherein the body-mountable electronic device is configured to be inserted into a deployment applicator.

12. The body-mountable electronic device of claim 11, further comprising:
    a wireless transceiver,
    wherein the detecting the signal comprises confirming the wireless transceiver establishes a wireless connection to a second device within the timeout period counted by the timer.

13. The body-mountable electronic device of claim 11, wherein the monitoring to detect the signal comprises monitoring to detect, via the sensor, a pattern of movements of the body-mountable electronic device.

14. The body-mountable electronic device of claim 11, further comprising:
    a biosensor configured to detect an analyte, wherein the monitoring to detect the signal comprises monitoring to detect a biosensor signal from the biosensor indicating detection of the analyte.

15. The body-mountable electronic device of claim 11, further comprising:
a communication interface,
wherein enabling the additional functionality comprises:
enabling collection of health data from a user upon which the body-mountable electronic device is deployed; and
enabling providing the health data to the user via the communication interface.

16. The body-mountable electronic device of claim 11, wherein the power source comprises a rechargeable energy storage device.

17. The body-mountable electronic device of claim 11, wherein the power source comprises a disposable energy storage device.

18. The body-mountable electronic device of claim 11, wherein the sensor is a motion sensor.

19. The body-mountable electronic device of claim 11, wherein the control circuitry comprises a microprocessor.

* * * * *